United States Patent
Gysling et al.

(10) Patent No.: US 6,837,098 B2
(45) Date of Patent: Jan. 4, 2005

(54) SAND MONITORING WITHIN WELLS USING ACOUSTIC ARRAYS

(75) Inventors: Daniel L. Gysling, Glastonbury, CT (US); Douglas H. Loose, Southington, CT (US)

(73) Assignee: Weatherford/Lamb, Inc., Houston, TX (US)

(*) Notice: Subject to any disclaimer, the term of this patent is extended or adjusted under 35 U.S.C. 154(b) by 35 days.

(21) Appl. No.: 10/392,493
(22) Filed: Mar. 19, 2003

(65) Prior Publication Data
US 2004/0182139 A1 Sep. 23, 2004

(51) Int. Cl.$^7$ .............................................. G01N 29/00
(52) U.S. Cl. ..................... 73/61.79; 73/61.47; 73/643
(58) Field of Search ..................... 73/61.79, 61.47, 73/61.49, 579, 643, 653, 656, 657

(56) References Cited

U.S. PATENT DOCUMENTS

| | | | |
|---|---|---|---|
| 3,149,492 A | 9/1964 | Weinberg | 73/724 |
| 3,851,521 A | 12/1974 | Ottenstein | 73/40.5 B |
| 4,080,837 A | 3/1978 | Alexander | 73/61.45 |
| 4,114,439 A | 9/1978 | Fick | 73/861.28 |
| 4,144,768 A | 3/1979 | Andersson | 702/140 |
| 4,159,646 A | 7/1979 | Paulsen | 73/861.28 |
| 4,164,865 A | 8/1979 | Hall | 73/861.28 |
| 4,236,406 A | 12/1980 | Reed | 73/61.45 |
| 4,275,602 A | 6/1981 | Fujishiro | 73/861.22 |
| 4,445,389 A | 5/1984 | Potzick | 73/861.27 |
| 4,499,418 A | 2/1985 | Helms | 324/637 |
| 4,515,473 A | 5/1985 | Mermelstein | 356/33 |
| 4,520,320 A | 5/1985 | Potzick | 327/7 |

(List continued on next page.)

FOREIGN PATENT DOCUMENTS

| | | |
|---|---|---|
| DE | 19511234 | 12/1995 |
| EP | 0684458 | 5/1995 |
| FR | 2 357 868 | 7/1976 |
| JP | 406082281 | 9/1992 |
| WO | WO 93/14382 | 7/1993 |
| WO | WO 96/04528 | 2/1996 |
| WO | WO 00/00793 | 1/2000 |

OTHER PUBLICATIONS

Apparatus for sensing fluid in a pipe, Davis et al. (US 2002/0064331) May 30, 2002.*

(List continued on next page.)

*Primary Examiner*—Hezron Williams
*Assistant Examiner*—Jacques M. Saint-Surin
(74) *Attorney, Agent, or Firm*—Moser, Patterson & Sheridan, L.L.P.

(57) ABSTRACT

A method for detecting the presence of particles, such as sand, flowing within a fluid in a conduit is disclosed. At least two optical sensors measure pressure variations propagating through the fluid. These pressure variations are caused by acoustic noise generated by typical background noises of the well production environment and from sand particles flowing within the fluid. If the acoustics are sufficiently energetic with respect to other disturbances, the signals provided by the sensors will form an acoustic ridge on a kω plot, where each data point represents the power of the acoustic wave corresponding to that particular wave number and temporal frequency. A sand metric then compares the average power of the data points forming the acoustic ridge to the average power of the data points falling outside of the acoustic ridge. The result of this comparison allows one to determine whether particles are present within the fluid. Furthermore, the present invention can also determine whether the generated acoustic noise is occurring upstream or downstream of the sensors, thus giving an indication of the location of the particles in the fluid relative to the sensors.

44 Claims, 4 Drawing Sheets

U.S. PATENT DOCUMENTS

| | | | |
|---|---|---|---|
| 4,546,649 A | 10/1985 | Kantor | 73/168 |
| 4,706,501 A | 11/1987 | Atkinson | 73/730 |
| 4,788,852 A | 12/1988 | Martin | 73/861.04 |
| 4,813,270 A | 3/1989 | Baillie | 73/861.04 |
| 4,862,750 A | 9/1989 | Nice | 73/861.24 |
| 4,864,868 A | 9/1989 | Khalifa | 73/861.24 |
| 4,884,457 A | 12/1989 | Hatton | 73/861.04 |
| 4,896,540 A | 1/1990 | Shakkottai | 73/861.02 |
| 4,932,262 A | 6/1990 | Wlodarczyk | 73/705 |
| 4,947,127 A | 8/1990 | Helms | 324/640 |
| 4,950,883 A | 8/1990 | Glenn | 250/227.14 |
| 4,976,151 A | 12/1990 | Morishita | 73/730 |
| 4,996,419 A | 2/1991 | Morey | 250/227.18 |
| 5,024,099 A | 6/1991 | Lee | 73/730 |
| 5,031,460 A | 7/1991 | Kanenobu | 73/730 |
| 5,040,415 A * | 8/1991 | Barkhoudarian | 73/198 |
| 5,051,922 A | 9/1991 | Toral | 700/285 |
| 5,058,437 A | 10/1991 | Chaumont. | 73/861.21 |
| 5,083,452 A | 1/1992 | Hope | 73/61.49 |
| 5,099,697 A | 3/1992 | Agar | 73/861.04 |
| 5,115,670 A | 5/1992 | Shen | 73/61.41 |
| 5,152,181 A | 10/1992 | Lew | 73/861.02 |
| 5,207,107 A | 5/1993 | Wolf | 73/861.04 |
| 5,218,197 A | 6/1993 | Carroll | 250/227.19 |
| 5,317,576 A | 5/1994 | Leonberger | 372/6 |
| 5,321,991 A | 6/1994 | Kalotay | 73/861.357 |
| 5,347,873 A | 9/1994 | Vander Heyden | 72/861.22 |
| 5,361,130 A | 11/1994 | Kersey | 356/478 |
| 5,363,342 A | 11/1994 | Layton | 367/149 |
| 5,367,911 A | 11/1994 | Jewell | 73/861.08 |
| 5,372,046 A | 12/1994 | Kleven | 73/861.22 |
| 5,398,542 A * | 3/1995 | Vasbinder | 73/40.5 A |
| 5,401,956 A | 3/1995 | Dunphy | 250/227.23 |
| 5,426,297 A | 6/1995 | Dunphy | 250/227.23 |
| 5,440,932 A | 8/1995 | Wareham | 73/730 |
| 5,493,390 A | 2/1996 | Varasi | 356/32 |
| 5,493,512 A | 2/1996 | Peube | 702/47 |
| 5,513,913 A | 5/1996 | Ball | 374/120 |
| 5,564,832 A | 10/1996 | Ball | 374/161 |
| 5,576,497 A | 11/1996 | Vignos | 73/861.22 |
| 5,591,922 A | 1/1997 | Segeral | 73/861.04 |
| 5,597,961 A | 1/1997 | Marrelli | 73/861.04 |
| 5,639,667 A | 6/1997 | Heslot | 436/148 |
| 5,642,098 A | 6/1997 | Santa Maria | 340/618 |
| 5,644,093 A | 7/1997 | Wright | 248/205.3 |
| 5,654,551 A | 8/1997 | Watt | 250/356.1 |
| 5,670,529 A | 9/1997 | Clarke | 73/730 |
| 5,680,489 A | 10/1997 | Kersey | 385/12 |
| 5,689,540 A | 11/1997 | Stephenson | 378/53 |
| 5,708,211 A | 1/1998 | Jepson | 73/861.42 |
| 5,730,219 A | 3/1998 | Tubel | 166/250.1 |
| 5,732,776 A | 3/1998 | Tubel | 166/250.15 |
| 5,741,980 A | 4/1998 | Hill | 73/861.04 |
| 5,803,167 A | 9/1998 | Bussear | 166/65.1 |
| 5,804,713 A | 9/1998 | Kluth | 73/152.01 |
| 5,842,347 A | 12/1998 | Kinder | 62/49.2 |
| 5,845,033 A | 12/1998 | Berthold | 385/12 |
| 5,906,238 A | 5/1999 | Carmody | 166/53 |
| 5,907,104 A | 5/1999 | Cage | 73/861.35 |
| 5,908,990 A | 6/1999 | Cummings | 73/861.24 |
| 5,925,821 A | 7/1999 | Bousquet | 73/592 |
| 5,925,879 A | 7/1999 | Hay | 250/227.14 |
| 5,939,643 A | 8/1999 | Oertel | 73/861.22 |
| 5,956,132 A | 9/1999 | Donzier | 356/133 |
| 5,959,547 A | 9/1999 | Tubel | 340/853.2 |
| 5,963,880 A | 10/1999 | Smith | 340/870.05 |
| 5,975,204 A | 11/1999 | Tubel | 166/250.15 |
| 5,992,519 A | 11/1999 | Ramakrishnan | 166/250.15 |
| 5,996,690 A | 12/1999 | Shaw | 166/250.01 |
| 6,002,985 A | 12/1999 | Stephenson | 702/13 |
| 6,003,383 A | 12/1999 | Zielinska | 73/861.2 |
| 6,003,385 A | 12/1999 | De Vanssay | 13/61.44 |
| 6,009,216 A | 12/1999 | Pruett | 385/12 |
| 6,016,702 A | 1/2000 | Maron | 73/705 |
| 6,158,288 A | 12/2000 | Smith | 73/861.25 |
| 6,216,532 B1 | 4/2001 | Stephenson | 73/152.21 |
| 6,233,374 B1 | 5/2001 | Ogle | 385/13 |
| 6,279,660 B1 | 8/2001 | Hay | 166/336 |
| 6,354,147 B1 | 3/2002 | Gysling | 73/61.79 |
| 6,378,357 B1 * | 4/2002 | Han et al. | 73/54.41 |
| 6,748,811 B1 * | 6/2004 | Iwanaga et al. | 73/861.27 |

OTHER PUBLICATIONS

U.S. patent application Ser. No. 10/115,727, Dec. 2002, Gysling, filed Apr. 3, 2002.

Mesch, F. (1990) "Speed and Flow Measurement by an Intelligent Correlation System", Advances in Instrumentation and Control, Research Triangle Park, NC, part 4, p. 1899–1914.

Gysling, D. (1999) "Development of a Fiber Optic Downhole Multiphase Flow Meter", in "Field Applications & New Technologies for Multiphase Metering", Multiphase Technology Series Conference, Aberdeen, Scotland.

Beranek, L. and Ver, I. (1992) in "Noise and Vibration Control Engineering, Principles and Application", John Wiley & Sons, Inc., Chapter 14, p:537–541.

Dowling, A. and Williams, J. in "Sound and Sources of Sound", Ellis Horwood Limited, Section 4, p:79–80.

Kersey, A. et al. (1993) "Multiplexed Fiber Bragg Grating Strain-Sensor System with a Fiber Fabry–Perot Wavelength Filter", Optics Letters, 18:1370–1372.

Dandridge, A. & Cogdell, G. (1991) "Fiber Optic Sensors for Navy Applications", IEEE, LCS, 2:81–89.

Nielsen, R. (1991) "Sonar Signal Processing", Artech Huse Inc., Chapter 2, p:51–59.

Krim A. and Viberg M. (1996) "Two Decades of Array Signal Processing Research", IEEE Signal Processing Magazine, p:67–94.

Kersey A. and Darkin, J., Editors (1992) SPIE vol. 1586, "Distributed and Multiplexed Fiber Optic Sensors", p:1–243.

Nerby et al. "A cost effective technique for production well testing", (1995) Offshore Technology Conference, p:505–515.

* cited by examiner

SAND MONITORING WITHIN WELLS USING ACOUSTIC ARRAYS

FIELD OF THE INVENTION

This invention relates generally to fluid sensing, and more particularly to detecting particles flowing in a fluid within a conduit.

BACKGROUND OF THE INVENTION

The production of particles, such as sand, concerns operators of oil/gas wells because of the possible catastrophic consequences on production. (In this disclosure, "sand should be understood as referring to solid particulate matter as would be found in an oil/gas well, without particular regard to its size or diameter). The production of sand may start at relatively minor levels, but then may rapidly increase resulting in clogged well lines that effectively "fill in" the well and halt production. Sand can also contaminate the separator tanks, which typically connect to other producing wells. When this occurs, the production of all oil wells feeding into the separator tanks must be halted. Furthermore, once sand has entered into the completion equipment, corrosion and/or erosion is likely, resulting in significant economic loss.

Operators will thus labor to avoid the production of sand completely, or at least attempt to detect sand at minor levels so that evasive action can be taken. By detecting sand at minor levels the operator may, for example, lower the rate of production (which might allow the sand to fall back through the well), reduce or cease completely any water injection, or in a multiple well system, shut down the affected well completely while allowing the other wells to continue production. In short, the onset of sand production is often the limiting factor in maximizing the production for a given oil and gas well. Because of the serious consequences associated with unnoticed sand production as described above, operators apply conservative production limits, which reduce the maximum production rates. Thus, a large incentive exists in the industry for methods of detecting sand quickly and continuously.

A variety of methods currently exist in the oil and gas industry to detect sand production. One such method is to physically filter a sample of produced fluids to check for solid particles. One problem with this method is that by the time the fluid has risen to the top of the well, it may be too late as contamination of the separator tanks and completion equipment may have already occurred. Furthermore, the filtering of selected samples will not detect sand continuously but instead only at designated time intervals. Therefore, this method is unlikely to detect sand at the inception of production when sand may most likely be encountered.

A technique that continuously monitors for sand production senses the vibrations caused by sand impacting the pipe or conduit in which the sand flows. These devices, such as a ClampOn™ meter, clamp on to, the pipe, typically at an "elbow" or section of the pipe where the fluid has to take an abrupt turn, and use ultrasonic detection methods to listen for the impact vibration of the sand. However, these ultrasonic methods typically only provide a qualitative measurement and are plagued with the difficulties associated with ultra high frequency coupling into the pipe. Furthermore, the device must be located near an elbow, thus would be unsuitable in the straight or slightly bent piping networks downhole. Although they have the benefit of continuous monitoring, they may also detect the presence of sand too late as they are practically limited to the surface environment.

Real-time monitoring of sand production would be valuable anywhere in the production string, but is particularly valuable downhole, i.e., in conjunction with the production tube, where sand would initially be produced before flowing to the surface. With the emergence of fiber optic sensors, continuous monitoring of fluids in the downhole environment is possible. Fiber Optic sensors and flowmeters already monitor parameters such as fluid sound speed, fluid velocity, pressure, and temperature. Such fiber optic based flowmeters are disclosed in the following U.S. Patent Applications and Patents, and are hereby incorporated by reference in their entireties: Ser. No. 09/740,760, entitled "Apparatus for Sensing Fluid in a Pipe," filed Nov. 29, 2000; Ser. No. 10/115,727, entitled "Flow Rate Measurements Using Unsteady Pressures," filed Apr. 3, 2002; and U.S. Pat. No. 6,354,147, entitled "Fluid Parameter Measurement in Pipes Using Acoustic Pressures," issued Mar. 12, 2002 [hereinafter referred to as the "flow meter references."]. The ability to reliably monitor sand production downhole in real-time, as the above parameters are currently measured, would allow for more effective management of sand production problems. Furthermore, coupling this capability with the real-time measurement of these other parameters results in a powerful fiber optic flowmeter for managing and optimizing well productivity.

The art would therefore benefit from a sensor that can be placed at any location along the production pipe and that can detect sand particles at minimal levels, thus allowing the operator to respond in an appropriate and timely manner to the production of sand.

SUMMARY OF THE INVENTION

A method for detecting the presence of particles, such as sand, flowing within a fluid in a conduit is disclosed. At least two optical sensors measure pressure variations propagating through the fluid. These pressure variations are caused by acoustic noise generated by typical background noises of the well production environment and from sand particles flowing within the fluid. If the acoustics are sufficiently energetic with respect to other disturbances, the signals provided by the sensors will form an acoustic ridge on a k$\omega$ plot, where each data point represents the power of the acoustic wave corresponding to that particular wave number and temporal frequency. A sand metric then compares the average power of the data points forming the acoustic ridge to the average power of the data points falling outside of the acoustic ridge. The result of this comparison allows one to determine whether particles are present within the fluid. Furthermore, the present invention can also determine whether the generated acoustic noise is occurring upstream or downstream of the sensors, thus giving an indication of the location of the particles in the fluid relative to the sensors.

BRIEF DESCRIPTION OF THE DRAWINGS

The foregoing and other features and aspects of the present disclosure will be best understood with reference to the following detailed description of embodiments of the invention, when read in conjunction with the accompanying drawings, wherein.

DETAILED DESCRIPTION OF EMBODIMENTS OF THE INVENTION

Figure 1:
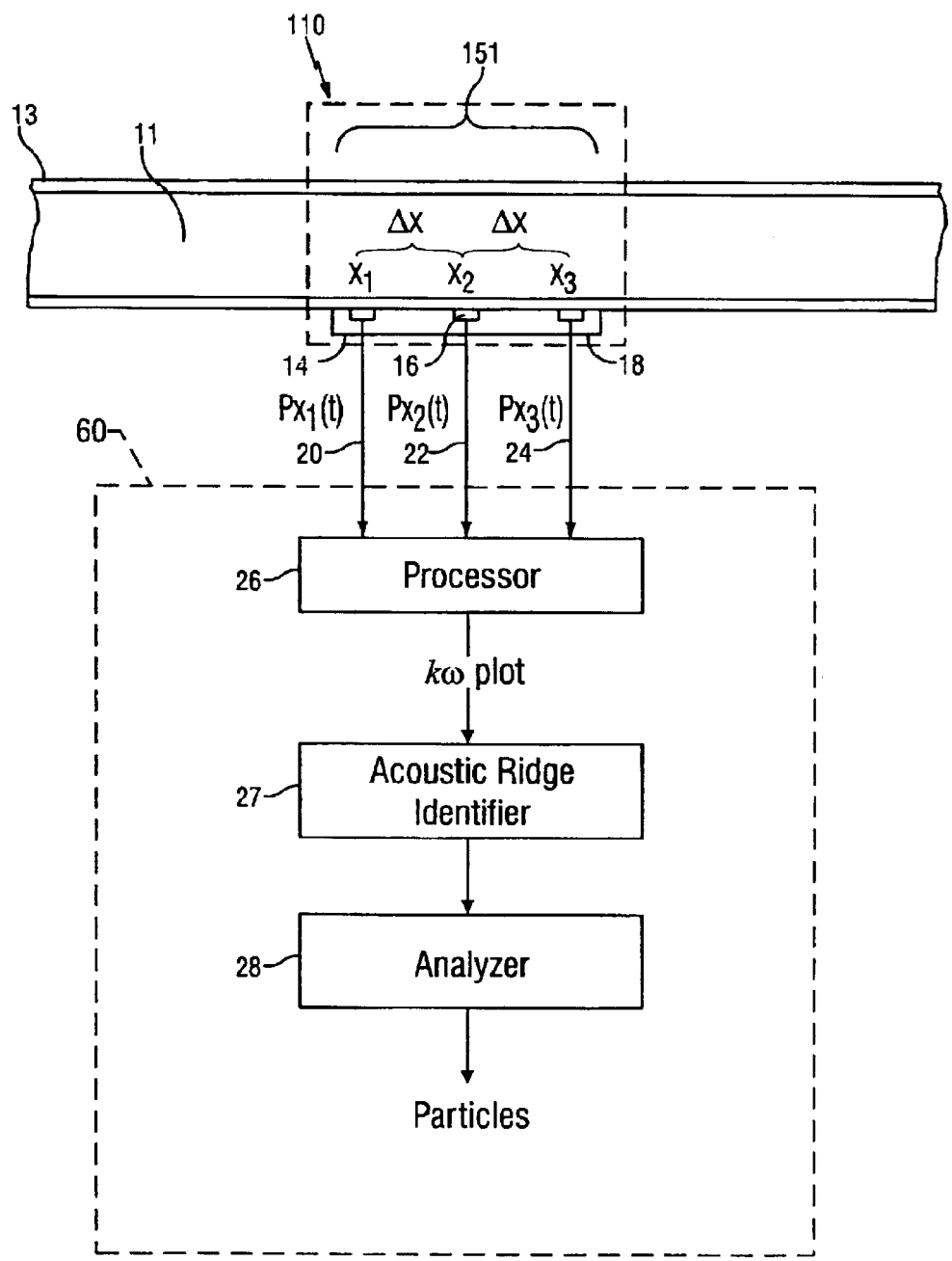
FIG. 1 illustrates a system for detecting the presence of particles in a fluid, according to the present invention.

In the disclosure that follows, in the interest of clarity, not all features of actual implementations are described in this disclosure. It will of course be appreciated that in the development of any such actual implementation, as in any such project, numerous engineering and design decisions must be made to achieve the developers' specific goals, e.g., compliance with mechanical and business related constraints, which will vary from one implementation to another. While attention must necessarily be paid to proper engineering and design practices for the environment in question, it should be appreciated that the development of a method to detect particles, such as sand, flowing within a conduit would nevertheless be a routine undertaking for those of skill in the art given the details provided by this disclosure, even if such development efforts are complex and time-consuming.

The present invention preferably uses a phased spatial array of optical sensors with Bragg gratings that measure acoustic pressure waves caused by sand particles propagating through the fluid. The sensors may measure the acoustic pressure waves by techniques disclosed in U.S. Pat. No. 6,354,147 entitled, "Fluid Parameter Measurement In Pipes Using Acoustic Pressures," or by sonar processing techniques disclosed in U.S. patent application Ser. No. 09/997,221 entitled, "Method And System For Determining The Speed Of Sound In A Fluid Within A Conduit," filed Nov. 28, 2001, both of which are incorporated herein by reference in their entirety. Furthermore, the optical sensors may comprise the acoustic sensing arrays found in the incorporated "flow meter references" listed above. By analyzing the power of the signals provided by the optical sensors through the use of a "sand metric," the present invention enables one to determine the presence of particles, such as sand, within the fluid.

Acoustic "background" noise is present within the fluid flowing within the production pipe. Such acoustics arise from a variety of sources, and can be useful in the detection of parameters of the fluid. For example, as disclosed in the incorporated "flow meter references," the naturally occurring pressure perturbations in the flowing fluid or fluid mixture can be used to determine, for example, the speed of sound, velocity, and other parameters of the fluid as previously mentioned. However, it has also been found that particles flowing within a fluid generate sufficient acoustic noise detectable over these other, more normal noises occurring within the fluid. Therefore, by analyzing the power of the acoustic signals, as will be discussed in more detail below, and by comparing that power with the power generated by other background noises, the presence of particles may be detected. A variety of interactions between the sand particles in a fluid cause this detectable acoustic noise, which occurs generally within the range of 100 Hz to 6,000 Hz, and more specifically, within the range of 200 Hz to 800 Hz. Mechanisms causing particle acoustic noise may include: (1) noise generated from the increased turbulence resulting from the fluid flowing over the multitude of particles, and (2) impact and scraping of the particles along the walls of the conduit.

Referring now to FIG. 1, a system according to the present invention for detecting particles in a fluid 11 flowing within a conduit 13 is shown. An array of pressure sensors 14, 16, 18 provide signals 20, 22, 24 indicative of the fluid pressure at each sensor location at a number of successive instants of time. (More sensors, or two sensors, could also be used). The array of sensors 14, 16, 18 measure the unsteady pressure disturbances within the fluid 11 caused by sand and other phenomenon propagating with or within the fluid. The sensors 14, 16, 18 may comprise fiber optic sensors and may further comprise any number of sensors equal to two or greater. The fiber optic sensors may coil around the conduit 13 in a series of wraps. As is disclosed in the above-incorporated "flow meter references," each wrap may be separated by a single Bragg grating for time division multiplexing (TDM) or each wrap may be separated by a pair of Bragg gratings for wavelength division multiplexing (WDM). However, other types of is pressure sensors, such as electrical or mechanical sensors, could be used with the present disclosure, again as disclosed in the "flow meter references."

As noted, the sensors 14, 16, 18 produce time varying pressure ($Px_i(t)$) signals indicative of the pressure of the acoustic disturbance detected at each of the sensors, in effect rendering information about pressure as a function of both location (x) and time (t), i.e., P(x,t). In a preferred embodiment useful in the detection of sand, these pressure signals are converted at processor 26 using well-known techniques into a kω plot, where k is wavenumber ($2\pi/\lambda$), and ω is the angular frequency ($2\pi f$). This conversion is affected at the processor 26 and preferably involves the use of well-known Fourier Transform algorithms. However, other spatial/temporal conversions (e.g., the generation of an xω plot, a kt plot, etc.) are also possible and useful with the disclosed technique, and "kω plot" should be understood as including these other types of spatial/temporal conversions. Because two variables (x and t) are transformed into two different variables (ω and k), a two-dimensional transform is utilized as one skilled in the art will understand. The well-known CAPON method, the MUSIC method, deterministic maximum likelihood methods, the minimum variance distortionless response method (MVDR) or MVDR beamformer methods, or other beamforming methods, are all preferred two-dimensional transforms useful in the present disclosure. The details of this conversion, the physics of wave propagation inside a pipe containing a fluid, and other considerations relevant to this technique, are disclosed in previously-incorporated U.S. patent application Ser. No. 09/997,221, and are not repeated here for simplicity.

Figure 2:
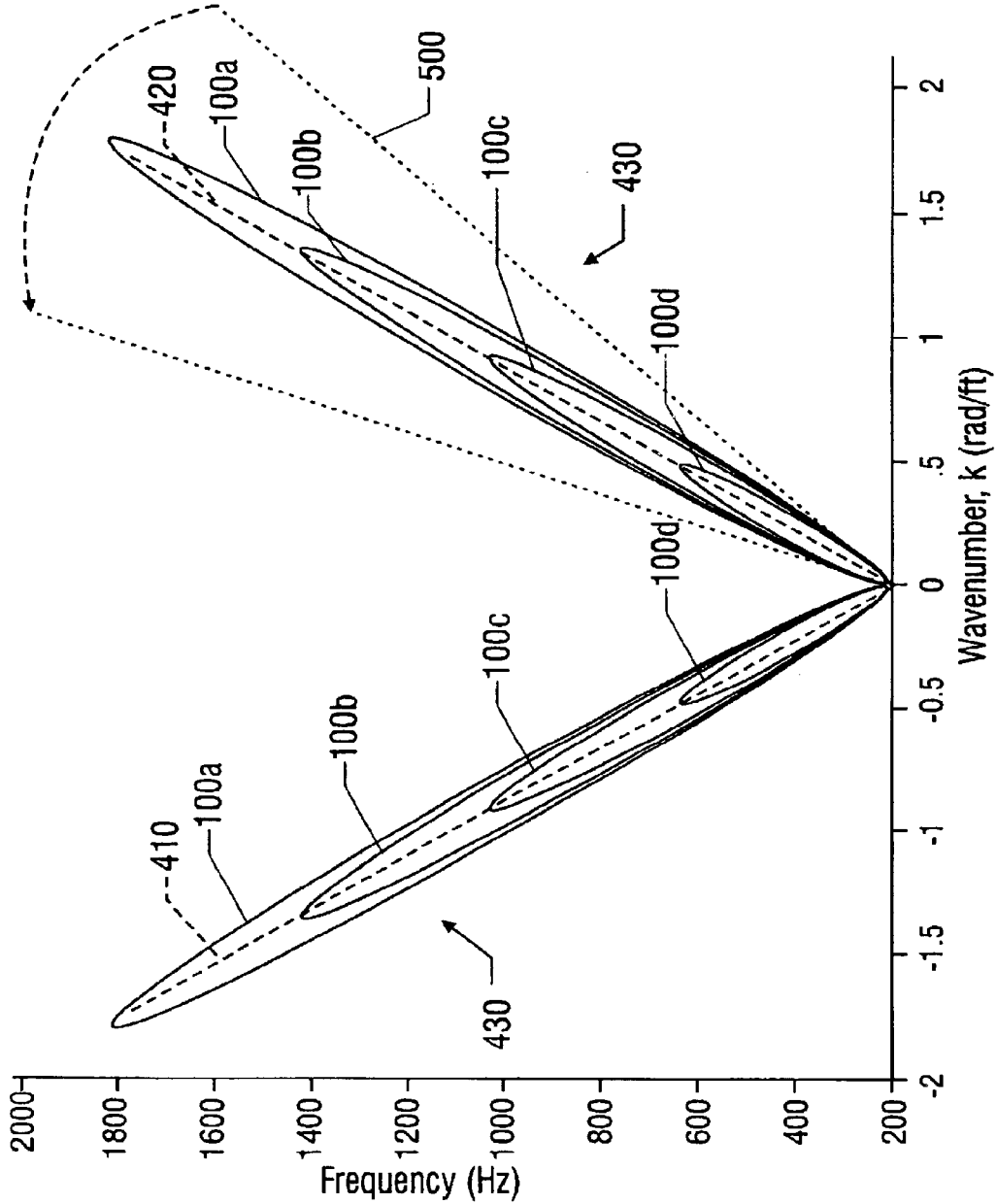
FIG. 2 illustrates a k$\omega$ plot with an acoustic ridge occurring above and below the meter, according to the present invention.

FIG. 2 shows an exemplary kω plot to be analyzed pursuant to the disclosed technique. The vertical axis of the plot is the temporal or angular frequency (ω) of the signal in rad/s and the horizontal axis is the spatial frequency or wave number (k) (e.g., in 1/ft). Each point (i.e., frequency) in the plot has associated with it a power level (in dB), as denoted by regions 100a–100d. In this regard, and in the computerized environment in which the kω plot is generated, it should be understood that the kω plot constitutes a data set in which each pixel comprises a particular power value, and not necessarily a visual plot.

Several different determinations about system acoustics can be made using the kω plot. First, it should be noticed that the accumulation of all of the acoustic events represented in the plot lie generally along straight lines, referred to as a "ridge" 430. This reflects the fact that all of the detected various acoustic events, each having its own unique frequency constitutions, travel through the fluid at approximately the same speed through the fluid, i.e., the fluid speed of sound. This fluid speed of sound, c, can therefore be calculated by computing a best fit line(s) 410, 420 within the ridge(s), and determining that line's slope, where ω=ck. (Dispersion, whereby the speed of sound in the fluid changes as a function of the frequency being transmitted, would cause this slope to deviate from linear, but significant dispersion should not occur with the frequencies of interest in a traditional oil/gas multiphase flow measurement, which ranges from approximately 10 Hz to approximately 2000 Hz). In short, the speed of sound in the fluid, c, can be calculated by using a kω plot, which can be useful in determining important parameters concerning the fluid being measured, such as its density or its phase fractions, as is noted in incorporated U.S. Pat. No. 6,354,147. (As noted in that patent and in the incorporated Ser. No. 09/997,221 application, pipe compliancy may need to be corrected for to determine the speed of sound in the fluid in an unbounded media, which might be a more useful parameter for certain applications). In an actual kω plot, a vertical ridge will also be apparent, but this is an artifact of various system noise and is not significant to determining the presence of sand or other system parameters. Hence, this vertical ridge is not shown in either FIG. 2 or FIG. 4 for clarity.

Second, and as shown in FIG. 2, the power of the various acoustic phenomena that are represented in the kω plot can be determined. Accordingly, regions 100a–100d represent areas of differing power levels, in which region 100d represents the highest power levels (e.g., 20 db), region 100c represents lower power levels (e.g., 10 db), etc. As one skilled in the art will understand, these power regions may be more uneven or blotchy in shape, and FIG. 2 shows only an idealized representation of the reflected power levels. As described below, an assessment of the power levels within a certain frequency range on the kω plot assists in determining the presence of sand.

Third, the kω plot allows for directionality of the acoustical disturbances to be determined. Referring to FIG. 1, the measured acoustics can arrive at the sensor array 110 as either left traveling-waves or right traveling waves, corresponding to energy on the left side or the right side of the kω plot. Because the speed of the fluid flowing within the pipe is usually much smaller than the speed of sound in the fluid, these left-traveling or right-traveling acoustic disturbances will approach the array 110 at approximately the same speed (assuming that the Mach number of the flow is <<1). Left-traveling disturbances will correspond to negative k values, while right-traveling disturbances correspond to positive k values. Thus, assuming that acoustics are being generated from both the left and the right of the array 110 as they would in when the fluid is flowing and acoustical disturbances are being created by sand and other natural phenomena in the fluid, the kω plot will exhibit two ridges 430, one along line 410, which is indicative of left traveling acoustics, and another along line 420, which is indicative of right traveling acoustics. Because the left-traveling and right-traveling waves arrive at approximately the same speed as mentioned above, the absolute value of the slopes of both lines 410, and 420 will be approximately equal, and both indicative of the speed of sound in the fluid.

The ridges 430 in the kω plot are assessed in the system by a computerized ridge identifier 27, as shown in FIG. 1, which can identify the ridges 430 using many known computerized techniques for assessing plots or plot data files. For example, the ridge identifier 27 can be preprogrammed with a power level threshold, in which pixels in the plot having values exceeding this threshold are deemed to constitute a portion of the ridge 430. Once the area of the plot containing the ridge 430 has been identified, its slope (i.e., lines 410 and 420) can be determined by analyzer 28, which preferably employs a weighted least squares fitting algorithms or other fitting algorithm well known in the art.

Referring still to FIG. 1, care should be taken to position the sensors 14, 16, 18 with suitable spacing (preferably, equally spaced by ΔX) for the application at hand to detect acoustical frequencies of interest. Of course, any particular acoustical phenomenon, such as those caused by sand, will comprise a plurality of frequency components. If a single frequency component is considered, the disclosed system obtains information about the wavelength λ (or the wavenumber k) of that frequency component essentially by sensing the phase of that component at (at least) any two of the sensors 14, 16, 18. Thus, the separation ΔX can be determined to be a particular fraction of a wavelength of the sound to be measured. The information is only not ambiguous, however, if the sensors sample frequently enough to avoid temporal aliasing, and are close enough to avoid spatial aliasing. For example, if the sensors are a distance ΔX apart that is two wavelengths of the frequency component being measured, the system may incorrectly indicate a value for the wavelength that is twice the actual value. Taking these practical limitations into account, it is preferred that the sensor 14, 16, and 18 be spaced at a distance ΔX of approximately eighteen inches apart, center to center, such as disclosed in the incorporated reference Ser. No. 09/740,760. Should it be necessary to resolve frequencies over a larger range than a single spacing distance would permit, additional sensors spaced at appropriate intervals could be added.

Sand creates acoustic phenomenon in the fluid which as noted travels at the speed of sound in the fluid, as do the other phenomena that are present or naturally occurring in the fluid. Accordingly, the acoustic phenomenon produced by the sand will lie along the same ridge 430 to which these other phenomena contribute. However, the presence of sand adds additional power to the acoustics in the fluid, and evidence suggests that it adds that power within a certain frequency range, e.g., between 200 to 800 Hz Accordingly, by assessing either or both of these effects, the presence of sand can be inferred. Moreover, and as facilitated by the use of fiber optic based flow meters, such detection can be performed continuously directly at the production pipe before sand reaches the top of the well.

As just noted, the presence of sand will add extra acoustic energy to the fluid flowing inside the pipe. Quantification of this energy, in one embodiment of the present invention, is performed by computation at analyzer 28 of a "sand metric" M that can be used to detect the presence of sand or to quantify the amount of sand present. In one embodiment, the sand metric computes the ratio of the average acoustical power along the ridge, $P_{acoustics}$, divided by the average acoustical power of some range outside of the ridge, $P_{non-acoustics}$. To normalize this embodiment of the sand metric, this ratio is subtracted by one so that the metric equals zero when no ridge is present, and is greater than zero when a ridge is present, i.e.:

$$M = \frac{P_{acoustics}}{P_{non-acoustics}} - 1$$

As one skilled in the art will realize, there are various ways by which the analyzer 28 can compute the power values to be used in the sand metric, and either average power values or summed power values may be used. In one embodiment, and referring again to FIG. 2, a straight line 500 passing through the origin at k=0 can be swept through a range of sound speeds (i.e., slopes) and the power of the various pixels in the kω plot can be summed (or averaged) along that line 500. When computing these summed or averaged powers, it is preferable to limit the analysis to frequencies where the acoustics generated from sand are likely to be found, such as from 200 Hz to 800 Hz, but may include other frequencies as well. Frequencies above and below this threshold range are preferably discounted.

Figure 3:
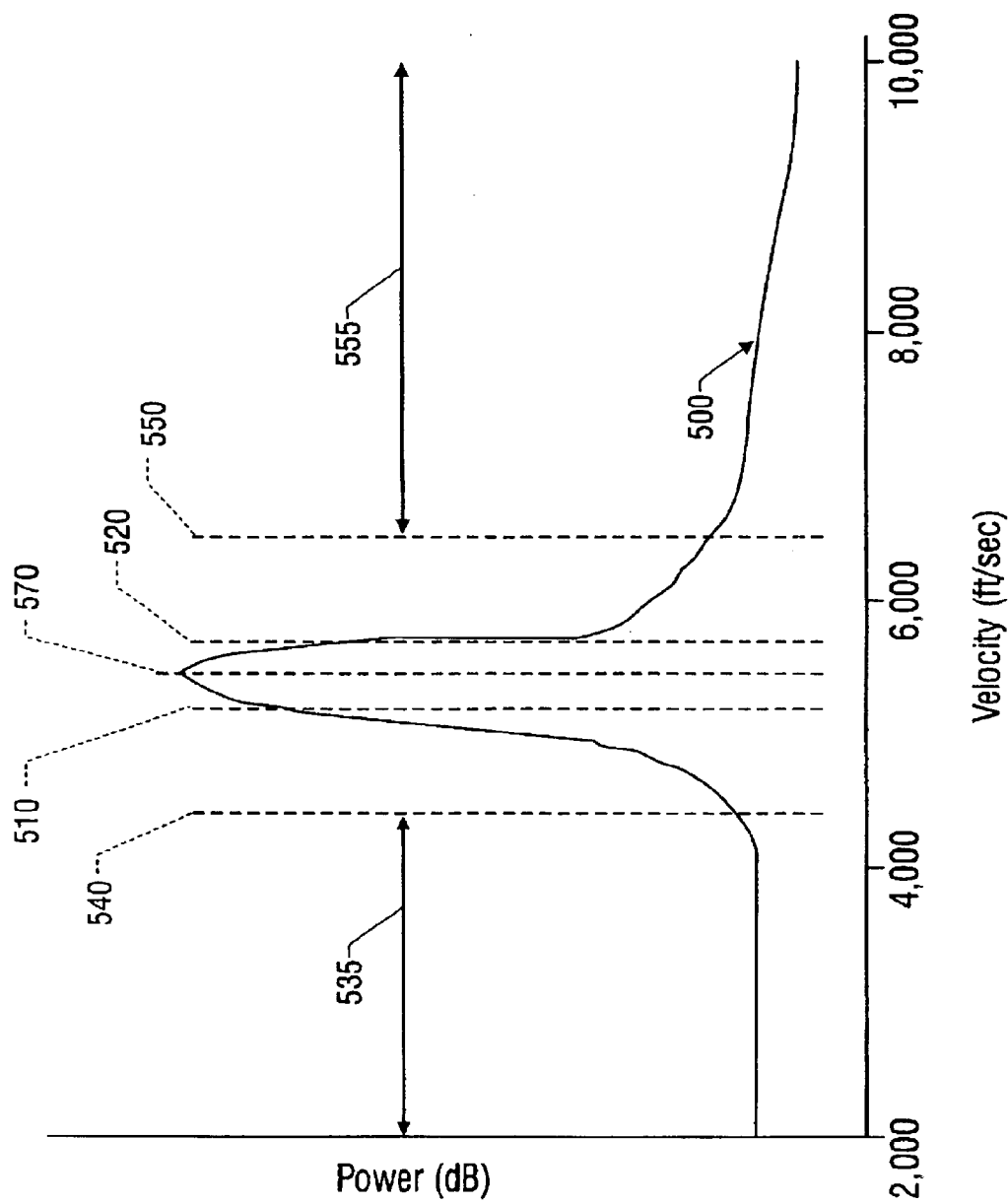
FIG. 3 illustrates a graph of power versus velocity with a peak corresponding to the fluid sound speed, according to the present invention.

FIG. 3 shows the results of this analysis for a sound speed range of 2,000 to 10,000 ft/sec. As expected, this graphs yields a power maximum 570 corresponding to the speed of sound in the fluid being analyzed for sand content, i.e., along line 420 of FIG. 2. (A similar analysis can be performed along line 410 as well). With this maximum located, the analyzer 28 can use various criteria to determine which speeds of sound correspond to the ridge (i.e., $P_{acoustics}$) and which fall outside that range (i.e., $P_{non-acoustics}$). For example, the maximum and minimum speeds of sound corresponding to power within the ridge, 520 and 510, may be defined as the full-width-half-maximum (FWHM) of the maximum 570, and may be defined according to set power levels (e.g., 30% of the maximum), or may be defined as a set range around the maximum. Likewise, the ranges 535 and 555 corresponding to the regions outside of the ridge, may be defined by limits 540 and 550 which are similarly related to the maximum, or which correspond to minimum power values, etc. After these limits are set, the values $P_{acoustics}$ and $P_{non-acoustics}$ can be calculated by summing or averaging the power values within these defined ranges. Of course, one skilled in the art will recognize that calculation of these power values for the sand metric can be calculated in any number of ways.

Once $P_{acoustic}$ and $P_{non-acoustic}$ and the sand metric M are calculated, the metric can be correlated to the presence of sand in any number of ways. In this regard, it is useful to remember that phenomena other than sand can contribute to the energy present at the ridge on the kω plot. Therefore, experimentation with or calibration of the pipe system being monitored may be necessary to understand when the sand metric is indicating the presence or quantity of sand. For example, suppose that an array deployed in operation consistently yields a sand metric of 10. If this value is seen to increase to a value of 12, and if detection of other parameters in the system cannot explain the increase acoustic energy, it may be inferred or at least contemplated that sand is being produced. Further verification of the presence of sand can then be performed, including techniques again employing the use of a kω plot as will be explained shortly. Correlation of the sand metric with other known sand detection techniques can also help to verify that the increase in the sand metric in fact correlates to sand production. For example, the flow meter before deployment can be calibrated using test equipment, such as a flow loop, and sand metric values can be calculated when the system is sand-filled or sand-free. Correlating the sand contents of sampled production fluids with the sand metric can further assist in determining normal values or ranges for the sand metric which would correlate to the production of sand. Other equations may be used to provide a sand metric that compares the ridge power to non-ridge based power, and the equation listed above should only be understood as exemplary.

It has proven difficult to test the utility of the disclosed apparatus and method to detect sand in a test flow loop, as the noise involved in a flow loop test apparatus has been seen to overwhelm the acoustics of sand introduced into the loop. However, data suggestive of the utility of the disclosed embodiments to detect sand is evidenced by an experiment which was performed on an actual working test well. In this test, a fiber optic based flow meter such as that incorporated herein was placed onto a production tube and lowered approximately 22,000 feet into a well suspected of producing sand. The well was activated to pump produced fluids to the surface. Production was then stopped, but the flow meter continued operation to monitor the acoustics within the production pipe.

Figure 4:
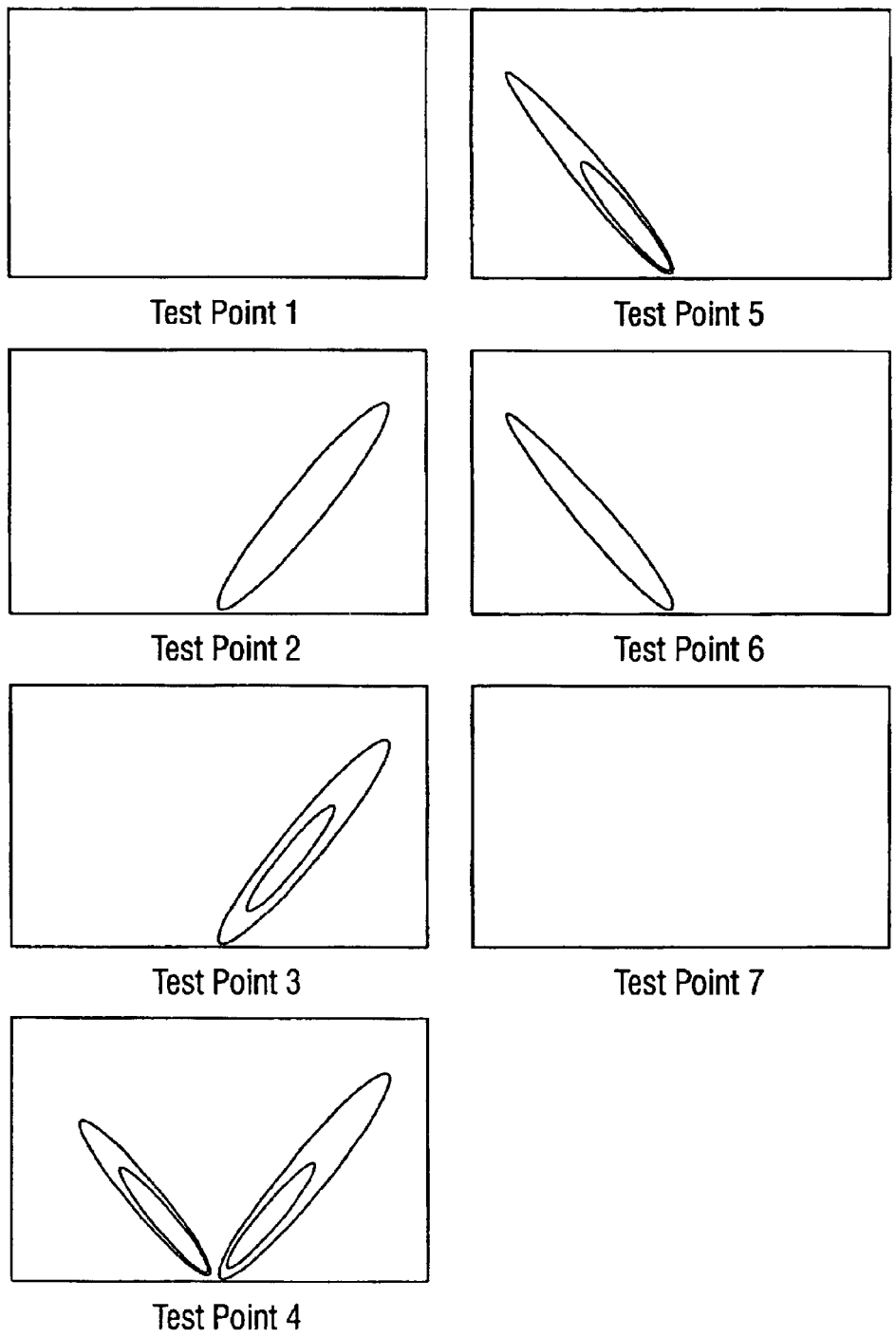
FIG. 4 illustrates kω plots suspected of indicating the presence of sand falling through a well whose production has been halted.

FIG. 4 illustrates the kω plots that were acquired at various times after production was halted. (The kω plots in FIG. 4, while indicative of actual data, are only exemplary, and have been simplified for illustration purposes). At the first test point 1 (time=0), no measurable acoustics were seen. Thereafter, at test point 2 (time=22 minutes later), a ridge appeared only on the right side of plot, which indicates that acoustics were being generated from some source above but not below the flow meter. The "top based" acoustics were seen to increase in power at test point 3 (time=31 minutes). At test point 4 (time=39 minutes), the acoustics were seen both above and below the flow meter. At test point 5 (time=43 minutes), the acoustics moved solely below the meter, and at test point 6 (time=61 minutes) the power of these "bottom based" acoustics dropped off to lower levels. At test point 7 (time=78 minutes), no appreciable acoustics were recorded.

It is theorized that the results seen in FIG. 4 are indicative of the presence of sand. Specifically, it is believed that a slug of sand was produced and was present near the top of the well after production was halted. Initially, the acoustics generated by this produced sand were not seen (test point 1) because they were too remotely located from the meter, and hence the sound generated by the sand was too attenuated by the time it reached the meter. However, as the sand fell back into the well due to gravity, it eventually approached the meter (test point 2), and the acoustical power generated by this sand increased as the sand came closer to the flow meter (test point 3). At test point 4, it is theorized that the falling sand had approached the meter, and to some extent exceeded past the meter as acoustics were now seen both above and below the flow meter. As the sand continued to fall past the meter, the power was seen only below the meter (test point 5), with decreasing power levels (test point 6), until the sand became too far away from the meter for its acoustics to be resolvable (test point 7).

It is hypothesized that the settling of produced sand could be the only cause of these results. Accordingly, the disclosed technique offers additional advantages for the detection of sand. If produced sand is suspected or detected while the well is producing, either using the disclosed sand metric or by other techniques, production can be temporarily halted to see if sand falls past the meter, i.e., if "top based" acoustics are seen followed by "bottom based" acoustics. Alternatively or in addition, the "top based" acoustics could be assessed to see if they increase in power over time, or the "bottom based" acoustics could be asses to see if they decrease in power over time. Although this constitutes an undesirable brief interruption in production, the interruption is only temporary, and would be worth the delay if the presence of sand can be verified, which might allow production to be varied to reduce the possibility of the continued production of sand. In short, the disclosed apparatus and techniques for detecting the presence of sand has utility both when the well is operational and fluid is flowing, and when production has been halted. If multiple meters are arrayed (e.g., multiplexed in series) along the production pipe, this method of determining the presence of sand can be redundantly verified, as the operator can listen for sand falling past the first meter, then the second meter, and so on.

The above-referenced test relies on the force of gravity to pull sand downward into the well, wherein the falling sand creates acoustic disturbances that are detectable by the flow meter. Accordingly, the detection technique that this test illustrates will perform best on wells or conduits that are vertical, although this is not strictly necessary.

"Directionally detecting" the acoustic disturbances in the fluid that are caused by sand should be understood as not merely determining the mere presence of acoustic disturbances. Instead, this phrase should be understood as meaning not only that acoustic are detected, but that their source is understood with relation to the flow meter that detects the disturbances, i.e., as either above or below the meter. As noted herein, the ability of the disclosed apparatus and methods to employ directional detection of acoustic phenomenon allows added flexibility over prior art approaches to fluid acoustic detection that merely detects acoustics without knowledge of its source.

Furthermore, $k\omega$ based processing applies temporal and spatial filtering techniques to increase the effective signal-to-noise ratio of sand generated acoustics, i.e., the disclosed method only considers the increase of acoustics propagating at the speed of sound of the fluid over a specific frequency range. Other signals with the sensor output such as electrical noise, vortical noise, impact noise propagating within the production tubing, are all effectively filtered out by the disclosed method.

It is contemplated that various substitutions, alterations, and/or modifications, including but not limited to those design alternatives which might have been specifically noted in this disclosure, may be made to the disclosed embodiment without departing from the spirit and scope of the invention as defined in the appended claims. For example, while particularly useful in detecting sand within a production pipe of an oil/gas well, the disclosed apparatus and method will have utility with respect to the detection of particulates in any pipe and in other industrial environments.

What is claimed is:

1. A method for detecting particles in a fluid within a conduit, comprising:
   placing at least two sensors along the conduit;
   measuring acoustic disturbances within the fluid using the sensors to produce at least two pressure signals;
   converting the pressure signals to form a data set indicative of the power of the pressure disturbances;
   computing a metric indicative of the presence of particles in the fluid using the data set, wherein the metric comprises a quantification of power within a frequency range attributable to the presence of the particles; and
   determining the presence of particles in the fluid based on the metric.

2. The method of claim 1, wherein the pressure signals are indicative of distance and time.

3. The method of claim 1, wherein the data set is indicative of the frequency and wavelength of the acoustic disturbances.

4. The method of claim 1, further comprising quantifying the particles in the fluid.

5. The method of claim 1, wherein the the frequency range is approximately 200 to 800 Hz.

6. The method of claim 1, wherein the metric comprises an assessment of the power traveling at the speed of sound in the fluid.

7. The method of claim 1, wherein the metric further comprises an assessment of the power traveling at the speed of sound in the fluid and the power not traveling at the speed of sound in the fluid.

8. The method of claim 1, wherein the data set comprises a $k\omega$ plot.

9. The method of claim 8, wherein computing the metric comprises identifying a ridge in the $k\omega$ plot, wherein the ridge corresponds to the acoustic disturbances that are traveling at the speed of sound in the fluid.

10. The method of claim 9, wherein computing the metric comprises computing an averaged or summed power along the ridge.

11. The method of claim 10, wherein computing the metric further comprises computing an averaged or summed power in a region outside of the ridge.

12. The method of claim 11, wherein the region outside of the ridge corresponds to a range of speeds of sound in the fluid.

13. The method of claim 11, wherein the metric comprises a calculation containing as variables (i) the averaged or summed power along the ridge, and (ii) the averaged or summed power in the region outside of the ridge.

14. The method of claim 1, wherein the sensors are coupled to an exterior surface of the conduit.

15. The method of claim 1, wherein the sensors are wrapped around the conduit.

16. The method of claim 15, wherein the sensors comprise fiber optic cable.

17. The method of claim 16, wherein the sensors each comprise at least one wrap of fiber optic cable.

18. The method of claim 17, wherein the sensors are serially coupled to fiber Bragg gratings.

19. A method for detecting particles in a fluid within a conduit using a flow meter coupled to the conduit, comprising in order:
   (a) ceasing the flow of fluid through the conduit;
   (b) directionally detecting acoustic disturbances within the fluid above the meter at a first time; and
   (c) directionally detecting acoustic disturbances within the fluid below the meter at a second time.

20. The method of claim 19, wherein directionally detecting the acoustic disturbances comprises the use of a $k\omega$ data set.

21. The method of claim 20, wherein step (b) comprises assessing the data set for a single ridge and wherein step (c) comprises assessing the data set for a single second ridge different from the first ridge.

22. The method of claim 21, wherein the acoustic disturbances lie along the first or second ridge.

23. The method of claim 19, wherein the acoustic disturbances travel at the speed of sound in the fluid.

24. The method of claim 19, wherein the flow meter comprises at least two sensors.

25. The method of claim 24, wherein the sensors are coupled to the outside of the conduit.

26. The method of claim 25, wherein the sensors comprise fiber optic sensors.

27. A method for detecting particle in a fluid within a conduit using a flow meter coupled to the conduit, comprising in order:
   (a) ceasing the flow of fluid through the conduit;
   (b) directionally detecting acoustic disturbances within the fluid above the meter at a first time and assessing a first power of the acoustic disturbances; and
   (c) directionally detecting acoustic disturbances within the fluid above the meter at a second time and assessing a second power of the acoustic disturbances, wherein the second power is greater than the first power.

28. The method of claim 27, wherein directionally detecting the acoustic disturbances comprises the use of a kω data set.

29. The method of claim 28, wherein the first and second powers in steps (b) and (c) are assessed along a ridge of the data set.

30. The method of claim 29, wherein the acoustic disturbances lie along the ridge.

31. The method of claim 27, wherein the acoustic disturbances travel at the speed of sound in the fluid.

32. The method of claim 27, wherein the flow meter comprises at least two sensors.

33. The method of claim 32, wherein the sensors are coupled to the outside of the conduit.

34. The method of claim 33, wherein the sensors comprise fiber optic sensors.

35. A method for detecting particle in a fluid within a conduit using a flow meter coupled to the conduit, comprising in order:
   (a) ceasing the flow of fluid through the conduit;
   (b) directionally detecting acoustic disturbances within the fluid below the meter at a first time and assessing a first power of the acoustic disturbances; and
   (c) directionally detecting acoustic disturbances within the fluid below the meter at a second time and assessing a second power of the acoustic disturbances, wherein the second power is less than the first power.

36. The method of claim 35, wherein directionally detecting the acoustic disturbances comprises the use of a kω data set.

37. The method of claim 36, wherein the first and second powers in steps (b) and (c) are assessed along a ridge of the data set.

38. The method of claim 37, wherein the acoustic disturbances lie along the ridge.

39. The method of claim 35, wherein the acoustic disturbances travel at the speed of sound in the fluid.

40. The method of claim 35, wherein the flow meter comprises at least two sensors.

41. The method of claim 40, wherein the sensors are coupled to the outside of the conduit.

42. The method of claim 41, wherein the sensors comprise fiber optic sensors.

43. The method of claim 19, further comprising determining a presence of the particles based on signals provided from detecting the acoustic disturbances within the fluid above the meter and the acoustic disturbances within the fluid below the meter.

44. A system for detecting particles in a fluid within a conduit, comprising:
   at least two sensors along the conduit, the sensors for detecting acoustic disturbances within the fluid;
   a processor for converting pressure signals from the at least two sensor into a data set;
   an analyzer for assessing the data set and computing a metric based on a quantification of power within a frequency range attributable to the presence of the particles; and
   an output based on the metric, wherein the output indicates the presence of particles in the fluid.

* * * * *